(12) United States Patent
Coelho do Sameiro Espregueira Mendes

(10) Patent No.: US 10,470,700 B2
(45) Date of Patent: Nov. 12, 2019

(54) MULTI-JOINT DEVICE FOR OBJECTIVE MEASUREMENT OF LAXITY AND CARTILAGE DAMAGE

(71) Applicant: ESPMEN—CONSULTORIA, UNIPESSOAL, LDA., Oporto (PT)

(72) Inventor: Joao Duarte Coelho do Sameiro Espregueira Mendes, Oporto (PT)

(73) Assignee: ESPMEN—CONSULTORIA, UNIPESSOAL, LDA., Oporto (PT)

( * ) Notice: Subject to any disclaimer, the term of this patent is extended or adjusted under 35 U.S.C. 154(b) by 595 days.

(21) Appl. No.: 15/118,719

(22) PCT Filed: Feb. 13, 2015

(86) PCT No.: PCT/IB2015/051077
§ 371 (c)(1),
(2) Date: Aug. 12, 2016

(87) PCT Pub. No.: WO2015/121830
PCT Pub. Date: Aug. 20, 2015

(65) Prior Publication Data
US 2017/0042465 A1 Feb. 16, 2017

(30) Foreign Application Priority Data

Feb. 14, 2014 (PT) .......................... 107467

(51) Int. Cl.
| A61B 5/00 | (2006.01) |
|---|---|
| A61B 6/03 | (2006.01) |
| A61B 5/055 | (2006.01) |
| A61B 5/103 | (2006.01) |
| A61B 6/04 | (2006.01) |

(52) U.S. Cl.
CPC ............ *A61B 5/4528* (2013.01); *A61B 5/055* (2013.01); *A61B 5/0555* (2013.01); *A61B 5/103* (2013.01); *A61B 5/4571* (2013.01); *A61B 5/4585* (2013.01); *A61B 5/4595* (2013.01); *A61B 6/032* (2013.01); *A61B 6/04* (2013.01);
(Continued)

(58) Field of Classification Search
CPC .............................. A61B 5/4528; A61B 5/702
See application file for complete search history.

(56) References Cited

U.S. PATENT DOCUMENTS

| 4,938,230 A | 7/1990 | Machek et al. |
| 6,684,095 B1 * | 1/2004 | Bonutti ................ A61B 5/0555 5/601 |

FOREIGN PATENT DOCUMENTS

| EP | 1219240 A2 | 7/2002 |
| EP | 2578150 A1 | 4/2013 |

OTHER PUBLICATIONS

International Search Report dated Jun. 24, 2015 for PCT/IB2015/051077.
Written Opinion dated Jun. 24, 2015 for PCT/IB2015/051077.

* cited by examiner

Primary Examiner — Omkar A Deodhar
(74) Attorney, Agent, or Firm — Lucas & Mercanti, LLP

(57) ABSTRACT

The present application discloses a medical device useful for the diagnosis and/or treatment follow-up of human joints, in particular a device for positioning human joints for CT-scan and MRI. The medical device allows an accurate and comprehensive assessment of human joints, characterizing quantitatively biomechanical consequences, whole joint
(Continued)

kinematics alterations, cartilage mechanical behavior under pressure and clinical susceptibility to further damage.

14 Claims, 3 Drawing Sheets

(52) U.S. Cl.
CPC .......... *A61B 6/0421* (2013.01); *A61B 6/0457* (2013.01); *A61B 6/0442* (2013.01)

MULTI-JOINT DEVICE FOR OBJECTIVE MEASUREMENT OF LAXITY AND CARTILAGE DAMAGE

CROSS REFERENCE TO RELATED APPLICATION

This Application is a 371 of PCT/IB2015/051077 filed on Feb. 13, 2015, which claims priority of Portuguese Application No. 107467 filed Feb. 14, 2014, both of which are incorporated herein by reference.

TECHNICAL FIELD

The present application discloses a medical device useful for the diagnosis and/or treatment follow-up of human joints, in particular a device for positioning human joints for CT-scan and MRI.

STATE OF THE ART

In recent decades, the number of injuries in sinovial joints like the ones present in human lower limbs has significantly increased. This problem affects both athletes and any other individuals who may be victims of accidents and/or congenital diseases.

This type of injuries and traumas leads to an individual inability since it creates instability within human joints, preventing their normal functions in the scope of static and dynamic stability as well in the scope of torque exertion in different joints lever systems, i.e. medial-lateral rotation, and proximal-distal translations of the hip; rotation, impulse and extension of the knee; patella stabilization, alignment and patella tracking in the femoral trochlea; varus and valgus of the ankle; inversion, eversion, anterior and posterior translation of the foot; thus creating an incapacity for the individual to execute his daily tasks, a significant increase of the risk of degenerative effects on the osteoarticular structures and a significant increase of the incidence of other and associated injuries.

The joints instability can be due to capsular ligamental deficiencies, inter-individual differences related to bone morphology of joints, neuromuscular dysfunctions, as well as due to the lower limbs alignment variations and hormonal influences.

In fact, the treatment, rehabilitation and/or prevention of disorders related to human joints varies depending on characterization, severity and complexity leading to different therapeutic and/or preventive approaches, ranging from conservative treatment to surgery.

Furthermore, in order to apply the appropriate treatment and/or preventive programs, it is essential to perform an accurate and precise diagnosis of the injury type.

Nowadays, the injury diagnosis is achieved through an inquiry presented to the patient, including questions like when and how the incident occurred, what type of activity was being executed and how often, as well as through inspection of the injured area and assessment of the injury both by clinical examination and imaging. However, these diagnostic tests, which may include radiographs (x-rays), computed tomography scan (CT-scan), magnetic resonance imaging (MRI) and arthroscopy, cannot accurately measure the severity of the injury, therefore lacking predictive and indicative value of additional health complications and therapeutic or preventive strategies, respectively. These limitations are extensive to the manual and visual clinical examination, which are even more likely to subjectivity.

Several mechanisms have been developed for the assessment of human joints. The following examples should be taken into account by their relevance in the area of this invention:

Devices KT1000 and KT2000 sold by MEDmetric® Corporation are known in the market and they roughly measure the anterior and posterior tibial translation, which is measured from the outside of the leg and has the muscle mass and other soft tissues, more or less compressible and variable from individual to individual, as an error factor, being this measurement taken only in mm. These devices are used only for evaluation of the anterior cruciate ligament rupture and posterior cruciate ligament rupture.

Telos device sold by Metax GmbH is known in the market and it allows separate measurements, only through x-ray technology, of the anterior and posterior tibial translation, as well as of the internal and external rotation of the tibia in which needs direct manual intervention, which allows some subjectivity, and it is hardly acceptable due to the radiation exposure. The device is used to evaluate the anterior talofibular and fibula-calcaneal ligaments, medial and lateral collateral ligaments of the knee, and the anterior and posterior cruciate ligaments, each ligament separately, just in extension and 90° position, not fully matching the clinically recommended positions of diagnosis.

Ferromagnetic materials are used in these devices, which makes them unsafe and incompatible with MRI or CT-scan devices. They interfere with the image processing and represent a risk for patient safety. Therefore, its use with MRI and CT-Scan is impracticable does not allowing the accurate examination of soft tissue structures.

SUMMARY

The present application discloses a device for measuring laxity of human joints with an imaging equipment, said joint being between a first proximal anatomic segment and a second distal anatomic segment, said device comprising a first part for support and fixation of the first anatomic segment, a second part for support and fixation of the second anatomic segment, and a force actuator which comprises at least two actuator push elements placed in opposite sides of the anatomic segment to be actuated, said actuator push elements being arranged to actuate independently.

In an embodiment, the first anatomic segment measured in the device is the hip, the second anatomic segment is the leg, and the joint is the hip joint, wherein the force actuator is arranged to cause medial or lateral rotation and/or proximal-distal translations of the hip.

In another embodiment, the first anatomic segment measured in the device is the leg, the second anatomic segment is the foot, and the joint is the ankle joint, wherein the force actuator is arranged to cause eversion or inversion of the ankle.

In even another embodiment, the first anatomic segment measured in the device is the leg, the second anatomic segment is the foot, and the joint is the ankle joint, wherein the force actuator is arranged to cause anterior or posterior drawer translation in the ankle joint.

In an embodiment, the first anatomic segment measured in the device is the hip, thigh, leg or patella, and the joint is, respectively, the hip joint, knee joint, ankle joint or patellofemoral joint, wherein the force actuator is arranged to cause compression of said joint.

In another embodiment, the force actuator introduced in the device is arranged to cause:

an external or internal rotation of the patella parallel to the coronal plane; or a lateral or medial translation of the patella parallel to the coronal plane; or a lateral or medial tilt of the patella relative to the coronal plane.

In even another embodiment, the device further comprising a second force actuator arranged to cause a lateral or medial tilt of the patella relative to the coronal plane, wherein the first force actuator is arranged to cause a lateral or medial translation of the patella parallel to the coronal plane, wherein said second force actuator is configured to actuate only after the first force actuator is actuating.

In an embodiment, the at least two actuator push elements of the device are placed in two opposite inner walls of the part for support and fixation of the anatomic segment to be actuated.

In another embodiment, the device comprises at least one scale placed in a part for support and/or fixation for indicating the position or angle of an anatomic segment relative to another anatomic segment.

In even another embodiment, the actuator used in the device comprises an inflatable element, in particular for inflating manually or by a compressor.

In an embodiment, the inflatable element used in the device is a hydraulic inflatable element, a pneumatic air cylinder or an inflatable bag.

In another embodiment, the first and second parts of the device are joined by sliding lockable joints, in particular lockable by tightening nuts.

In even another embodiment, the device comprises a flat base for providing support and stability on the horizontal plane to said device, wherein the flat base is attached to the sides of the first and second parts by tightening nuts.

In an embodiment, the imaging equipment of the device is a computed tomography scan or a magnetic resonance imaging.

In another embodiment, the device is made of polymers, resins, composites, or mixtures thereof.

The present application also discloses a Magnetic Resonance Imaging equipment or Computer Axial Tomography equipment comprising the device previously disclosed.

The present application discloses the use of the device for the measure of hip internal-external rotation and proximal-distal translations, tibial anterior-posterior translation, internal-external rotation of the knee, medial-lateral patella translation, medial-lateral patellar tilt, internal-external patellar rotation, varus and valgus talar tilt within the ankle joint, anterior-posterior translation of the foot, inversion and eversion of the foot and multi-axis coaptation of all the above mentioned joints.

GENERAL DESCRIPTION

It is disclosed a medical device for accurate and direct quantification of human joints damage through cartilage coaptation, as well as the measurement of dynamic and/or static laxity i.e., abnormal movement patterns of injured joints, like hip, knee and patellofemoral, foot and ankle joints, inside the CT-scan and MRI devices. This medical device is MR Safe and MR compatible allowing cartilage mechanical properties assessment through coaptation and laxity quantification in all planes and axes of motion of human joints, simultaneously with MRI and CT-scans.

The device can be placed inside a MRI or CT-scan device to measure laxities due to injuries of human joints like hip, knee, foot and ankle in order to obtain at least one image of antero-posterior, medial-lateral, proximal-distal translations, rotations and concomitantly combined movements patterns, which may be measured between two bony points with high precision.

The results obtained by this device constitute important clinical information for treatment, rehabilitation and prevention purposes by using and identifying them as criteria and/or risk factors within follow-up in clinical or ecologic sets of patients.

The device now disclosed on this application allows an accurate and comprehensive assessment of human joints, characterizing quantitatively biomechanical consequences, whole joint kinematics alterations, cartilage mechanical behavior under pressure and clinical susceptibility to further damage. This ability has the utmost clinical relevance, since it configures the information the physicians need in order to avoid, for instance, cartilage injuries, which treatment represents unestimated costs for national health services and negative impact on the life quality and social-professional domains. Objective assessment, which is reachable by means of the present invention, helps define exactly who are the patients that will need surgery and those which only require conservative treatment and/or prevention programs.

The device is a solution for measuring joints instability, from which standard objective criteria arise for subsequent treatment algorithm establishment. This device covers main articular complexes which are under epidemiologic constant surveillance and represents the larger number of musculoskeletal pathologies and lesions among general population, amateur and professional sports.

The device described in this application allows an accurate measuring, i.e. empirically an error comprised between 1 or 2 mm, or 1 or 2 degrees, depending on the sharpness of the technician, of for instance: hip internal-external rotation (FIG. 1-*a*); tibial anterior-posterior translation, internal-external rotation of the knee (FIG. 1-*b*); medial-lateral patella translation, medial-lateral patellar tilt and internal-external patellar rotation (FIG. 1-*c*); varus and valgus talar tilt within the ankle joint, anterior-posterior translation of the foot, inversion and eversion of the foot (FIG. 1-*d*) which are combined movements of adduction, suppination and plantar flexion and abduction, pronation and dorsiflexion, respectively; multi-axis coaptation of all the above mentioned joints; being in every case possible to measure accurately all the referred human joints movements combined and at the same time, since it can be used inside devices of MRI or CT-scan, not interfering with image processing because it doesn't include ferromagnetic materials. Actually, the device includes safe and compatible materials for MRI and CT-scan such as inter alia, composites, plastics, resins and carbon fibers.

With the broad positioning ability of the device described in this application, the measurements are made in the images from MRI and CT-scan between bone structures such as: acetabulum and femur; femur and tibia; patella and tibia, femur and patella; talus and tibia, tibia and fibula; fibula and talus, calcaneus and fibula, calcaneus and tibia, calcaneus and talus; and others under the broad concept of instability measuring within MRI and CT-Scan.

These measurements can be correlated to associated injuries observed in the images, like inter alia, with ligaments, menisci, cartilages, etc. Besides that, the findings can constitute important clinical information for treatment, clinical follow-up, rehabilitation and prevention purposes.

The device is useful for example for ruptures of the iliofemoral, pubofemoral and ischiofemoral ligaments of the hip; anterior cruciate ligament and posterior cruciate ligament, anterolateral ligament of the knee, antero-external, postero-external, antero-internal, postero-internal and medial-lateral instabilities, instabilities in all directions, and also to evaluate all possible rotational instabilities of the knee. It is also capable of evaluating instabilities in all directions of the foot and ankle such those resulting from medial collateral and lateral collateral ligaments of the ankle and intrinsic ligaments of the foot joints, i.e. ligaments with insertion within foot bones contributing for passive stabilization of foot joints.

The device also allows the evaluation of axial coaptation of ankle and knee joints, as well as of other mechanisms for hip coaptation, which are important for studying mechanical function and behaviour of joints cartilage.

This device has advantages that include:

Until now, with prior art technique, the instability measurement is made roughly and by approximation, while, with this present device it will be possible to measure human joints instability with accuracy. Furthermore, through its structure and functioning, being totally compatible for MRI or CT-scan use and in obtaining and measuring bone dislocation, in all planes and axes, of normal and abnormal human joints, allowing accurate and direct quantification of their dynamic (different movements combined) and/or static laxity. A technical solution like this device and associated quantification methods was repeatedly claimed in the scientific literature as the very needed "gold standard", i.e., a technical solution with methods and abilities to quantify dynamic and/or static laxity concomitantly with MRI or CT-scan.

Until now, the treatment and surgeries for human joints injuries were generic. With this present device it will be possible to get and set a real diagnosis, leading to more appropriate treatments which means one can decide whether or not to perform surgery with greater precision, and can choose between different types of conservative treatment or surgery depending on the needs, leading to a higher success rate in patients' recovery, resources managing and saving and better quality of life and health for patients.

BRIEF DESCRIPTION OF THE FIGURES

The following figures provide preferred embodiments for illustrating the description and should not be seen as limiting the scope of invention.

Figure 1:
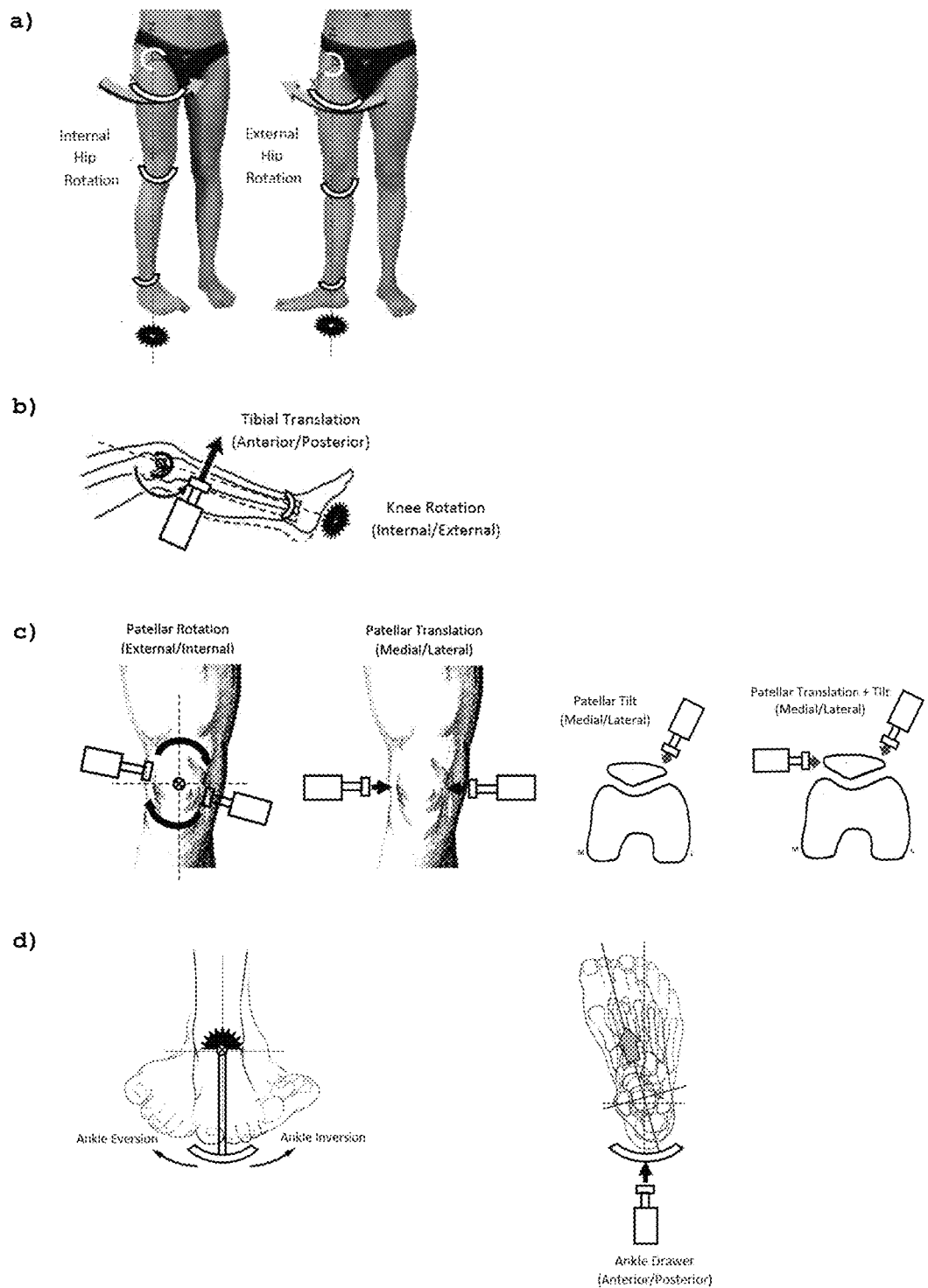
FIG. 1—device diagrams of the movements applied to the (a) hip and knee and (b, c) patellofemoral joints and (d) foot and ankle joints, provided by the device.

Wherein the reference numbers refer to:

(1) represents a device for measuring the instability of human joints, in particular knee and patellofemoral, foot and ankle joints;
(2) represents a part for posterior support and fixation of the thigh;
(3) represents a part for posterior support and fixation of the leg;
(4) represents a supporting piece;
(5) represents a part for posterior-plantar-lateral support and fixation of the foot;
(6) represents moving parts with flat bases;
(7) represents articulation elements;
(8) represents a removable part for posterior and front fixation of the leg;
(9) represents a removable part for positioning onto the patella;
(10) represents a removable part to adjust the means to each patient (15) and the removable part for positioning onto the patella (9);
(11) represents a removable supporting part;
(12) represents sliding elements to adjust the device to the leg length of each patient;
(13) represents means to execute the rotational movements of the ankle and the foot in clockwise and anticlockwise direction;
(14) represents means to push the foot forward;
(15) represents means to push the patella medially or laterally and/or to tilt the patella;
(16) represents means to push the leg posteriorly and anteriorly;
(17) represents means to adjust and support the removable supporting part (11);
(18) represents tightening nuts for the moving parts (6), for the articulation elements (7) and for the removable supporting part (11).

DESCRIPTION OF EMBODIMENTS

The present application discloses a medical device useful for the diagnosis and/or treatment follow-up of human joints. Specifying some applications, the medical device is useful for accurate and direct quantification of hip, knee and patellofemoral, foot and ankle joints dynamic and/or static laxity i.e., abnormal movement patterns of the referred injured joints, as well as for the evaluation of their cartilage mechanics through coaptation. This medical device is MR and CT-scan Safe and MR Compatible allowing in the scope of human joints the quantification of ligaments and cartilage damage. The present device allows measurements of static and/or dynamic joint laxities in all planes and axes of motion; static laxity is measured involving only one degree of freedom of the joint, whereas dynamic laxity measurements consider the whole joint kinematics. Additionally, the device enhances the visualization and measuring of bone morphometrics and soft tissues (eg.: femur and its trochlear groove depth).

Figure 2:
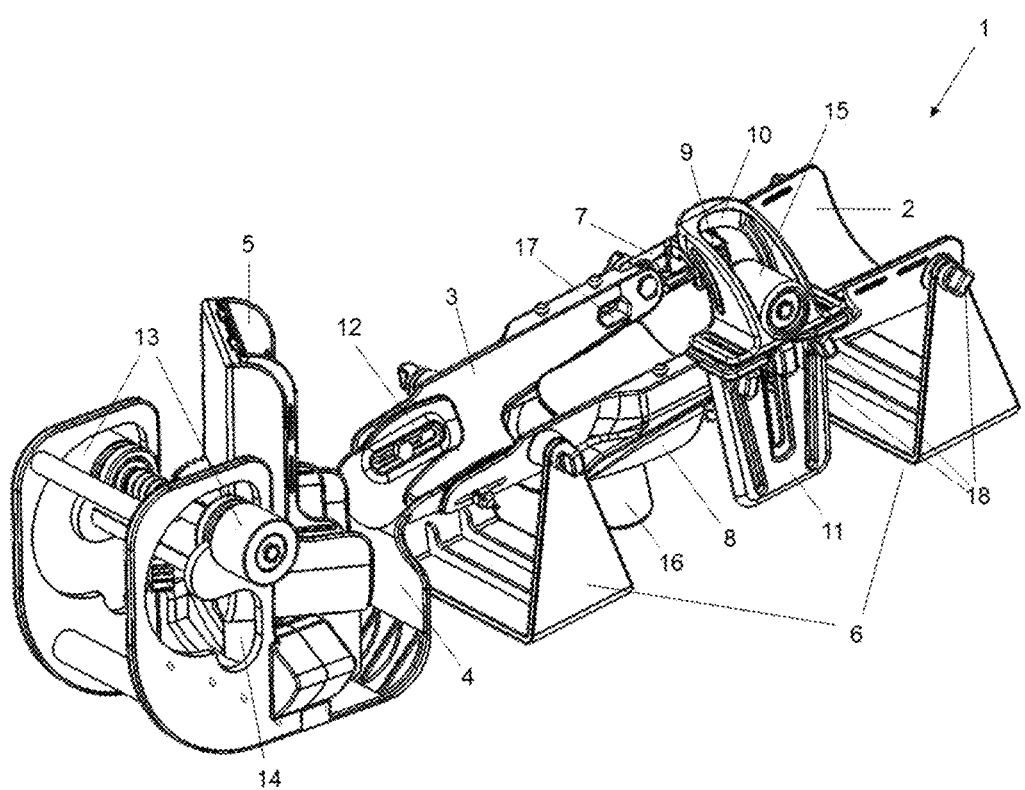
FIG. 2—schematic representation of a preferred embodiment where it is represented a perspective view of the device for thigh, leg and foot anatomic segments, thus knee and ankle joints, and patella.
Figure 3:
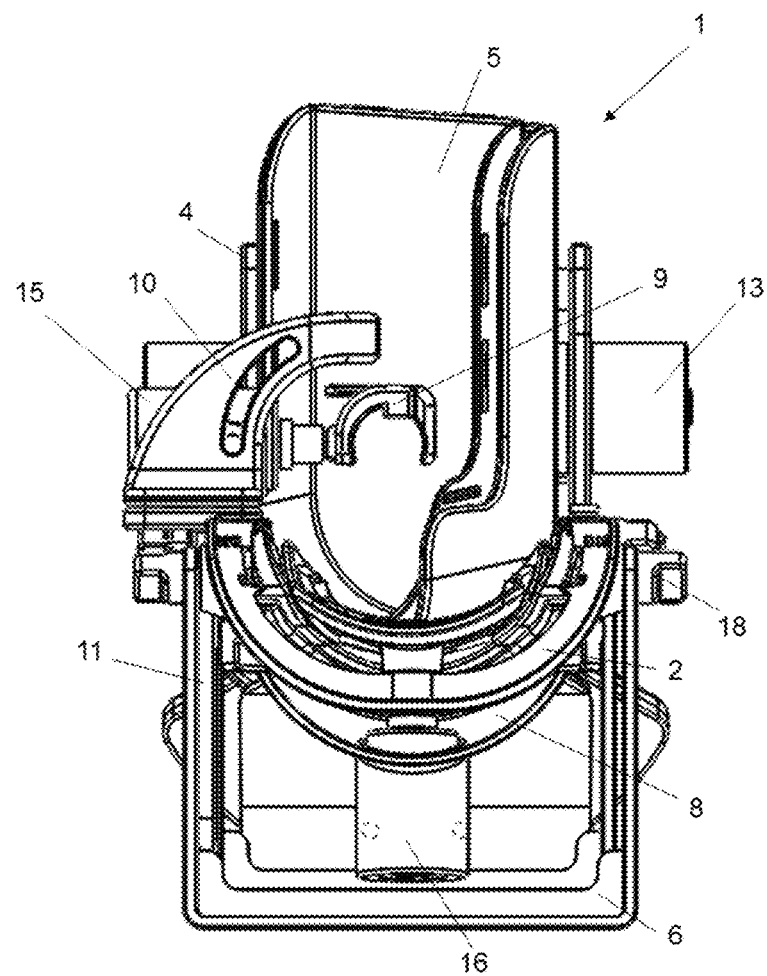
FIG. 3—schematic representation of a preferred embodiment where it is represented a front view of the device for thigh, leg and foot anatomic segments and patella.

As can be seen in FIGS. 2 and 3, a particular embodiment of the device for measuring human joints (1) described is comprised by parts, namely a part for the posterior support and fixation of the thigh (2), a part for the posterior support and fixation of the leg (3), a supporting part (4) and a part for posterior-plantar-lateral support and fixation of the foot and ankle (5).

These parts may respectively include multiple belts, not represented in the figures, which together with additional parts (8) ensure that the leg, thigh and foot lay and remain fixed against the device (1). Other restraining means are also possible, as straps, girdles, fasteners, cuffs, clamps, or removable parts.

The device comprises at least two actuator push elements placed in opposite sides of the anatomic segment to be actuated, said actuator push elements being arranged to actuate independently. Independently of the human joint to be measured, the force actuators are equal to each other.

To ensure that the images obtained with the device (1) by imaging equipment, in particular by computed axial tomography scan or magnetic resonance imaging, do not show distortions, all materials used in the device are not ferromagnetic, preferably polymers, resins, composites, among others.

The device (1) comprises independent means (16) to push backwards or forward, towards the leg, respectively the anterior or posterior zone of the leg, shown in FIG. 2, respectively located in the inner wall of a part (8) for posterior or anterior support and fixation of the leg. One or both parts are preferably removable.

The device also includes a part for positioning the device onto the patella (9) containing means (15) to push the patella medially or laterally and/or to tilt the patella and/or to rotate the patella, which are adjusted and supported by the parts (10 and 11) attached on the articulation elements (7) in particular through tightening nuts (18), as shown in FIG. 2, allowing to test the patellar movements in any position of the articulated device.

Example measurements of clinical relevance of the patellofemoral joint include measurements of both angles and displacements caused by the force means of the present device, as is detailed further below. This also applies to other joints—the layout and design of the presently disclosed force means enable the evaluation of joint laxity in both angles and displacements, thus making possible measurements that improve the observability of relevant clinical circumstances.

The displacements the device promotes by applying pressure also allow better distal femoral epiphyseal and patellar morphometric measurements, such as trochlear groove depth, crossing sign, lateral trochlear inclination, trochlear facet asymmetry, by exposure of bone landmarks and soft tissues ability to restraint motion is also measured in the scope of diagnosis and or clinic follow-up after conservative or surgical treatments.

On the other hand, in the foot zone (4), as can be seen in FIG. 3, the device also comprises means (13) that are able, respectively alternating through vertical and horizontal shafts, to push the foot and to push the ankle, in multiplanar motions, in clockwise and anti-clockwise direction, as well as means (14) to push the foot forward and backward, strategically located into the support piece (4).

These means (13, 14, 15 and 16), denominated actuators, to move their respective foot and ankle, patella and leg zones, so as to position and hold the patient foot and/or patella and/or leg into position, can be of any suitable kind, namely manually inflatable bags or compressor filled ones, or by hydraulic means, or by spring-loaded elements, and can work independently and alternatively from each other.

The device allows the release of the actuators in order to the accurate and safe application of the test, preventing the application of excessive force onto the anatomical structures.

Moreover, the means (16) to push their respective leg zones can work in conjunction with the means (13) to push the foot, so as to position and hold the foot and/or the patient's leg into position. This combined movement is an advantageous feature of the device. It is also an advantageous feature of the device to make it combined simultaneously with a MRI or CT-scan equipment.

Thus, as described, the device can position, hold and move the foot and/or the patella and/or the leg and/or the thigh of the patient in various positions, from −10° to 50°0 degrees of knee flexion.

The measurements performed with the device (1) include the evaluation in mm and/or degrees of translation and/or rotation into the MRI or CT-scan device, or any other imaging device that permits these measurements. These measurements are normally taken with no pressure and then with pressure, wherein a certain loading is applied on a given anatomic segment, considering the bony landmarks of its respective joint. It is important to refer that from the movements induced by the present device combined with the compatibility with imaging devices, one can get more than a single measurement: taking in consideration the example of the patellofemoral joint evaluation, from a loading applied on the medial facet of the patella along the medial-lateral axis (lateral patellar translation), one can measure either its lateral displacement considering the distance from the medial edge of the patella to a line drawn perpendicular to the posterior condylar line and passing through the most anterior point of the medial femur condyle; either its lateral tilt considered as the angle between the posterior condylar line and a line drawn through the maximum width of the patella. Similar procedure is translated to the other referred joints, in order to characterize the whole joint's movements.

The device is manually or automatically placed over the examination table of the MRI or CT-scan equipment. Through the visualization of the MRI or CT-scan images, one can evaluate the condition of the tissues that ideally resist dislocation and promote alignment of the anatomical structures of the mentioned joints.

The device (1) includes scales to initially indicate the position of the leg and/or patella and/or foot, both in mm and/or degrees of translation and/or rotation.

In the device, the parts of the leg and thigh can be positioned at different angles between their own, in particular comprised between −10 and 50 degrees, through the articulation elements (7) held in the desired positions by suitable means, for example tightening nuts (18), clamps, ratchets. The parts of the leg and thigh can also be adapted to various anatomical dimensions of the patient by sliding said elements (12) and parts (2, 3 and 4) which are then fixed in the desired positions by mechanical fixing means, not represented in the Figures, placed in openings or holes existing in those elements and parts. Through the same sliding system, the piece (9) for positioning onto the patella, removable part (9) and supporting part (10) can identically be adapted to various anatomical dimensions of the patella of each patient, as well as to different anatomical positions of the patella on the patient's knee and also to the various positions of the device through the articulated elements (7).

In FIGS. 2 and 3 one can see the moving parts (6) comprising flat bases which will provide support and stability to the device (1) on a horizontal plane. These moving parts (6) are fastened to the sides of parts (2) and (3) through tightening nuts (18).

The disclosure is of course not in any way restricted to the embodiments described and a person with ordinary skill in the art will foresee many possibilities to modifications thereof without departing from the basic idea of the disclosure as defined in the appended claims.

The above described embodiments are obviously combinable.

The following dependent claims set out particular embodiments of the disclosure.

The invention claimed is:

1. A device for facilitating measurement of laxity of a human joint with an imaging equipment, the device comprising:

a first part, adapted to receive and hold a thigh, the first part including one or more first belts adapted to hold the thigh;

a second part adapted to receive and hold a portion of a leg;

a first element attached to the second part, the first element adapted to cause movement of an anterior zone of the leg;

a second element attached to the second part, the second element adapted to cause movement of a posterior zone of the leg;

a third part adapted to receive and hold a foot, the third part including one or more second belts; and at least one third element attached to the third part, the at least one third element adapted to cause rotational movement of the third part in a first angular direction and in a second angular direction.

2. The device according to claim 1 further comprising a force actuator adapted to cause one of:

an external or internal rotation of a patella parallel to a coronal plane;

a lateral or medial translation of the patella parallel to the coronal plane; or a lateral or medial tilt of the patella relative to the coronal plane.

3. The device according to claim 2 further comprising a second force actuator arranged to cause a lateral or medial tilt of the patella relative to the coronal plane, wherein the first force actuator is arranged to cause a lateral or medial translation of the patella parallel to the coronal plane, wherein said second force actuator is configured to actuate only after the first force actuator is actuating.

4. The device according to claim 1 wherein first element is disposed on a first inner wall of the second part and the second element is disposed on a second inner wall of the second part.

5. The device according to claim 1 comprising at least one scale disposed in one of the first part, the second part, and the third part, the scale adapted to a position or angle of a first body part relative to a second body part.

6. The device according to claim 1, wherein one of the first element, the second element, and the at least one third element comprises an inflatable element.

7. The device according to claim 6, wherein the inflatable element is one of a hydraulic inflatable element, a pneumatic air cylinder and an inflatable bag.

8. The device according to claim 1, wherein the first and second parts are coupled by a plurality of sliding lockable joints adapted to be locked by tightening nuts.

9. The device according to claim 1 further comprising a flat base attached to the first and second parts, the flat base being adapted to provide support and stability in a horizontal plane to the device.

10. The device according to claim 1, wherein the imaging equipment is one of a computed tomography scan device and a magnetic resonance imaging device.

11. The device according to claim 1 wherein the device comprises one of polymers, resins, composites, and mixtures thereof.

12. A magnetic resonance imaging device comprising the device of claim 1.

13. A method comprising:

using the device of claim 1 to measure one of hip internal-external rotation and proximal-distal translations, tibial anterior-posterior translation, internal-external rotation of a knee, medial-lateral patella translation, medial-lateral patellar tilt, internal-external patellar rotation, varus and valgus talar tilt within an ankle joint, anterior-posterior translation of a foot, inversion and eversion of a foot and multi-axis coaptation of a joint.

14. A computer axial tomography device comprising the device of claim 1.

* * * * *